US006916951B2

(12) United States Patent
Tustin et al.

(10) Patent No.: US 6,916,951 B2
(45) Date of Patent: Jul. 12, 2005

(54) CONTINUOUS CARBONYLATION PROCESS

(75) Inventors: Gerald Charles Tustin, Kingsport, TN (US); Regina Michelle Moncier, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 116 days.

(21) Appl. No.: 10/434,596

(22) Filed: May 9, 2003

(65) Prior Publication Data

US 2003/0212295 A1 Nov. 13, 2003

Related U.S. Application Data

(63) Continuation-in-part of application No. 10/140,226, filed on May 6, 2002, now abandoned.

(51) Int. Cl.[7] .................... C07C 69/02; C07C 67/36; C07C 51/10; C07C 51/12; C07C 51/54
(52) U.S. Cl. .................. 560/231; 560/232; 562/517; 562/519; 562/890
(58) Field of Search ................................ 560/231, 232; 562/517, 519, 890

(56) References Cited

U.S. PATENT DOCUMENTS

| 3,689,533 A | 9/1972 | Schultz |
| 3,717,670 A | 2/1973 | Schultz |
| 3,772,380 A | 11/1973 | Paulik et al. |
| 4,333,884 A | 6/1982 | Kubbeler et al. |
| 4,358,411 A | 11/1982 | Porcelli et al. |
| 4,366,259 A | 12/1982 | Knifton et al. |
| 4,417,077 A | 11/1983 | Drago et al. |
| 4,430,273 A | 2/1984 | Erpenbach et al. |
| 5,144,068 A | 9/1992 | Smith et al. |
| 5,258,549 A | 11/1993 | Pimblett |
| 5,298,586 A | 3/1994 | Beevor et al. |
| 5,488,143 A | 1/1996 | Uhm et al. |
| 5,510,524 A | 4/1996 | Garland et al. |
| 5,900,505 A | 5/1999 | Tustin et al. |
| 6,211,405 B1 | 4/2001 | Cheung et al. |

FOREIGN PATENT DOCUMENTS

| EP | 0 081 152 A | 6/1983 |
| EP | 0 109 212 A | 5/1984 |
| EP | 0 153 834 | 9/1985 |
| EP | 0 338 730 A1 | 10/1989 |
| EP | 0 391 680 | 10/1990 |
| EP | 0 584 964 | 3/1994 |
| EP | 0 752 406 | 1/1997 |
| EP | 0 976 711 A1 | 2/2000 |
| EP | 1 364 936 A1 | 11/2003 |
| GB | 2 029 409 A | 3/1980 |
| JP | 146933 A | 5/2003 |

OTHER PUBLICATIONS

*Catalysis Today,* 18, (1993) 325–354.
Fujimoto et al. in *Chemistry Letters* (1987) 895–898.
Journal of Catalysis, 133 (1992) 370–382.
Welton in *Chemical Reviews* 99 (1999) 2071–2083.
Knifton in *J. Catal.,* 96, (1985) 439–453.
*Green Chemistry* 3 (2001) 76–79.
*Chem. Int. Ed. Engl.* 34 (1995) 2698–2700.
*Catalysis Letters,* 2 (1989) 145–148.
Wasserscheid, Peter and Keim, Wilhelm, 'Ionic Liquids—New "Solutions" for Transition Metal Catalysis', *Angew. Chem. Int. Ed.,* 2000, 39, pp. 3772–3789.

*Primary Examiner*—James O. Wilson
*Assistant Examiner*—Zachary C. Tucker
(74) *Attorney, Agent, or Firm*—Eric D. Middlemas; Bernard J. Graves, Jr.

(57) ABSTRACT

Disclosed is a continuous process wherein carbon monoxide, a carbonylatable reactant, and a halide in the gas phase are contacted with a non-volatile catalyst solution comprising an ionic liquid and a Group VIII metal to produce a carbonylation product in the gas phase. The process is useful for the continuous preparation of acetic acid by the carbonylation of methanol.

22 Claims, No Drawings

CONTINUOUS CARBONYLATION PROCESS

CROSS REFERENCE TO RELATED APPLICATIONS

This application is a continuation-in-part of application Ser. No. 10/140,226, filed May 6, 2002 now abandoned, incorporated herein by reference.

FIELD OF THE INVENTION

This invention pertains to a process for the preparation of carbonylation products. More specifically, this invention pertains to a continuous, vapor-phase process for the preparation of carboxylic acids, esters, anhydrides, and mixtures thereof by contacting carbon monxide, a halide promoter, and carbonylatable reactant with a liquid catalyst solution comprising an ionic liquid and a Group VIII metal.

BACKGROUND OF THE INVENTION

Processes for the manufacture of acetic acid from methanol by carbonylation are operated extensively throughout the world. A thorough review of these commercial processes and other approaches to accomplishing the formation of acetyls from single carbon sources is described by Howard et al. in *Catalysis Today*, 18 (1993) 325–354. All commercial processes for the preparation of acetic acid by the carbonylation of methanol presently are performed in the liquid phase using homogeneous catalyst systems comprising a Group VIII metal and iodine or an iodine-containing compound such as hydrogen iodide and/or methyl iodide. Rhodium is the most common Group VIII metal and methyl iodide is the most common promoter. These reactions are conducted in the presence of water to prevent precipitation of the catalyst. The catalyst precipitation is a serious problem during the flashing process whereby the liquid products exiting the carbonylation reactor are subjected to a partial release in pressure. The pressure release causes vaporization of a portion of the products and a decrease in the temperature resulting from the heat of vaporization. If too much water is removed during the flashing process, precipitation of the rhodium catalyst will occur. U.S. Pat. No. 5,144,068 describes the inclusion of lithium in the catalyst system which allows the use of less water in the Rh-I homogeneous process.

The precipitation of the catalyst is reduced through the use of quaternary phosphonium or quaternary ammonium iodides as soluble components in liquid phase carbonylation processes for catalyst promotion and catalyst stabilization in catalyst purification processes. U.S. Pat. No. 4,430,273 describes a process for making acetic anhydride from the carbonylation of methyl acetate in the presence of a Group VIII metal in a carboxylic acid solvent containing a heterocyclic quaternary nitrogen compound. U.S. Pat. No. 4,333,884 describes a process for making acetic anhydride from the carbonylation of methyl acetate in the presence of a Group VIII metal in a carboxylic acid solvent containing a heterocyclic quaternary nitrogen or phosphorous compound and a zirconium compound. The processes described in U.S. Pat. Nos. 4,430,273 and 4,333,884 require a carboxylic acid solvent component and are operated in a mode where the product is removed from the reaction zone as a liquid.

The troublesome flash process can be avoided by conducting the carbonylation reaction in the vapor-phase using heterogeneous catalysts. Schultz, in U.S. Pat. No. 3,689,533, describes the use of supported rhodium as a heterogeneous catalyst for the carbonylation of alcohols to carboxylic acids in the vapor phase in the presence of a halide promoter. In U.S. Pat. No. 3,717,670, Schultz describes a similar supported rhodium catalyst in combination with promoters selected from Groups IB, IIIB, IVB, VB, VIB, VIII, (current notations: 11, 3, 4, 5, 6 and 8–10 respectively) lanthamide and actinide elements of the Periodic Table. Uhm, in U.S. Pat. No. 5,488,143, describes the use of alkali, alkaline earth or transition metals as promoters for supported rhodium for the halide-promoted, vapor phase methanol carbonylation reaction. A serious problem associated with vapor phase carbonylation reactions using solid phase catalysts is the removal of the heat of reaction. Since the thermal conductivity of vapor is much less than that of the corresponding liquid, the reactor used in a vapor phase process must have a high surface area to facilitate the removal of the heat of reaction. The complexity and cost of these high surface area reactors negates much of the potential beneficial aspects of vapor phase carbonylation processes.

Ionic liquids have been used as solvents for synthetic reactions and transistion metal-catalyzed processes including carbonylation reactions. A review of ionic liquids is provided by Welton in *Chemical Reviews* 99 (1999) 2071–2083. Knifton et al. in U.S. Pat. No. 4,366,259 describe a process for the preparation of acetic and propionic acid by homologation of carbon monoxide in the presence of hydrogen and a ruthenium-cobalt catalyst system dispersed in a low-melting phosphonium or ammonium salt. The selectivity of this process toward either acetic or propionic acid was low. In addition, this process was conducted under batch conditions and required extended reaction times, high temperatures, and high pressures. Such forcing conditions would make this carbonylation process difficult and uneconomical to operate. Tanaka et al., in *Green Chemistry* 3 (2001) 76–79, describe the palladium-catalyzed carbonylation of aryl halides with alcohols in the ionic liquid 1-butyl-3-methylimidazolium tetrafluoroborate or hexafluorophosphate. The process of Tanaka et al. does not avoid many of the catalyst handling and processing disadvantages encountered in traditional liquid phase carbonylation processes.

The liquid phase carbonylation processes discussed above require separation of the volatile reaction products and starting materials from the less volatile catalyst components by distillation from the reaction vessel or by flashing of the reaction solution at reduced pressures. These separation processes are frequently complicated, require expensive corrosion resistant equipment, involve extensive recycle and processing of catalyst residues, and often result in loss of catalyst values. Heterogeneous processes avoid the flash process but cannot remove heat at a sufficient rate to attain high production rates. Thus, there is need for a carbonylation process which provides for simple product separation while maintaining a stable catalyst environment and gives high reaction rates with efficient heat removal from the reaction zone.

BRIEF SUMMARY OF THE INVENTION

In accordance with the present invention, we have discovered a novel continuous process for preparing a carbonylation product comprising the following steps:

I. continuously feeding to a reaction zone carbon monoxide, a carbonylatable reactant, and a halide selected from chlorine, bromine, iodine and compounds thereof, wherein said carbon monoxide, carbonylatable reactant, and halide are in the gas phase;

II. continuously contacting said carbon monoxide, carbonylatable reactant, and halide of Step I with a non-volatile catalyst solution comprising an ionic liquid and a Group VIII metal under steady state carbonylation conditions and at a temperature and pressure wherein said carbonylation product exits said reaction zone in the gas phase; and III. continuously recovering from the reaction zone a gaseous effluent comprising the carbonylation product.

Our process provides advantages over other carbonylation processes in that vapor phase reactants are contacted with a non-volatile catalyst solution instead of a solid, supported catalyst or a liquid reaction mixture containing substantial amounts of volatile components, such as the liquid reactants and products. The present invention is useful as a continuous process for the preparation of acetic acid comprising:

I. continuously feeding to a reaction zone carbon monoxide, methyl alcohol, and methyl iodide, wherein said carbon monoxide, methyl alcohol, and methyl iodide are in the gas phase;

II. continuously contacting said carbon monoxide, methyl alcohol, and methyl iodide of Step I with a non-volatile catalyst solution comprising about 50 to about 100 wt % of an ionic liquid selected from a quaternary ammonium salt or a quaternary phosphonium salt, and rhodium while maintaining said reaction zone at a temperature of about 150 to about 240° C. and a pressure of about 3 bara to about 50 bara; and III. continuously recovering from said reaction zone a gaseous effluent comprising acetic acid, methyl acetate, or a mixture thereof.

Another embodiment of the present invention is a continuous process for the preparation of acetic acid wherein the ionic liquid is methyltributylphosphonium iodide, butyltridodecylphosphonium iodide, 1-butyl-3-methylimidazolium iodide, or 1,3-dimethylimidazolium iodide.

The process of the present invention solves many of the problems encountered in liquid and vapor phase carbonylation processes in that the reactants are fed in the vapor phase, contact a catalyst solution comprising an ionic liquid and a Group VIII metal, and the products exit the reaction zone in the vapor phase. The catalyst solution, comprising an ionic liquid and Group VIII metal, provides greater heat removal efficiency than traditional vapor-phase processes using solid catalysts and a more stable catalyst environment that reduces or eliminates the need for catalyst recovery and recycle. Our novel process provides high reaction rates and simplifies product purification. The present invention also provides a means for carbonylation of alcohols that requires no water addition to the reactant stream.

DETAILED DESCRIPTION OF THE INVENTION

The present invention is a process for the preparation of carbonylation products wherein the carbon monoxide, a halide and a carbonylatable reactant in the gas phase are contacted with a non-volatile catalyst solution comprising an ionic liquid and a Group VIII metal in a reaction zone to produce a carbonylation product in the gas phase. Our novel process solves the problems encountered with heat removal in heterogeneous, vapor phase carbonylation processes and the problems associated with catalyst stability in homogeneous processes. The catalyst solution provides greater heat removal efficiency than traditional vapor-phase processes using solid catalysts and a more stable catalyst environment that reduces or eliminates the need for catalyst recovery and recycle. Our novel process provides high reaction rates and simplifies product purification. A general embodiment of the instant invention involves (1) continuously feeding carbon monoxide, a carbonylatable reactant, and a halide in the gas phase to a reaction zone; (2) continuously contacting the carbon monoxide, carbonylatable reactant, and halide in the reaction zone with a non-volatile catalyst solution comprising an ionic liquid and a Group VIII metal under steady state carbonylation conditions and at a temperature and pressure wherein the carbonylation product exits the reaction zone in the gas phase; and (3) continuously recovering a gaseous effluent comprising the carbonylation product.

Our process produces a carbonylation product. The term "carbonylation product", as used herein, is well-understood by persons skilled in the art, and is intended to mean one or more organic compounds produced by the insertion of carbon monoxide into one or more chemical bonds of a reactant. Typical carbonylation products are carboxylic acids, esters, and anhydrides. The carbonylation product of the present invention is not intended to be limited to a single product, but may include multiple products. For example, the process of the invention converts alcohols into carboxylic acids and esters. Olefinic alcohols my be converted in lactones. In the substantial absence of water, ethers are converted into carboxylic esters and anhydrides. In the presence of sufficient water, ethers are converted into carboxylic acids and esters. In the substantial absence of water, esters are converted into carboxylic acid anhydrides. In the presence of sufficient water, esters are carbonylated to give carboxylic acids, which may react with any alcohols that are present (from hydrolysis of the starting ester) to produce additional esters.

The temperature and pressure of the reaction are chosen such that reactants enter the reaction zone in the vapor phase, and products and unconverted reactants leave the reaction zone in the vapor state. Throughout the present invention, the terms "vapor phase", "gaseous", "vapor state", "vaporous", "gaseous state", and "gas phase" are used interchangeably and are intended to be synonymous. The non-volatile catalyst solution comprises an ionic liquid and a Group VIII metal. In addition to the ionic liquid, the catalyst solution may contain varying amounts of other reaction components such as, for example, unconverted reactants, reaction products, dissolved carbon monoxide, dissolved hydrogen, and the like. According to our invention, the catalyst solution is substantially non-volatile, that is, at steady state and under process conditions of temperature and pressure, the catalyst solution remains in the reaction zone and is not transported out of the reaction zone with the products or unconverted reactants. Thus, the term "non-volatile", as used herein in reference to the catalyst solution, means that the catalyst solution contains a concentration of ionic liquid sufficient to enable the process of the present invention to be operated at steady state and under carbonylation conditions of temperature and pressure wherein the weight of gaseous reactants entering the reaction zone substantially equals the weight of gaseous products and unconverted reactants exiting the reaction zone. The term "steady state", as used herein, means a condition where the process parameters, e.g., temperature, pressure, mass flows, of any part of the process are constant during operation of the process. Under steady state conditions, therefore, the catalyst solution may be maintained at a substantially constant volume within the reaction zone, without substantial absorption or condensation of volatile reactants and reaction products.

Typically, the concentration of ionic liquid in the catalyst solution at steady state may be in the range of about 25 to about 100 weight % (abbreviated herein as "wt %") based on the total weight of the catalyst solution, and is dependent, inter alia, upon the ionic liquid and the process conditions of temperature, pressure, and conversion of carbon monoxide. For example, the concentration of other liquid components, such as reaction products and unconverted reactants, is governed in part by their equilibrium concentrations between the ionic liquid and the gas phase at a specified temperature and pressure. Under some process conditions, for example, the concentration of ionic liquid may approach 100 wt %. In this embodiment, the catalyst solution has low or negligible vapor pressure, both at ambient conditions of room temperature and atmospheric pressure and at carbonylation reaction conditions, and is substantially free of volatile or solubilizing liquid components, such as liquid reactants and products. At other conditions of temperature, pressure, and conversion, however, the catalyst solution may comprise additional liquid components such as carbonylation products, unconverted reactants, etc. At these conditions, for example, the concentration of ionic liquid within may be in the range of about 50 to about 100 wt %. Further representative examples of ionic liquid concentration ranges are about 60 to about 100 wt %, about 75 to about 100 wt %, and about 90 to about 100 wt %.

The concentration of ionic liquid may be measured by sampling the catalyst solution at steady state and measuring the concentration of the various components by gas chromatography, liquid chromatography, ion-exchange chromatography, or other techniques well known to those skilled in the art. Alternatively, a sample of the catalyst solution may be subjected to gas stripping or stripping at reduced pressures to separate any reaction components from the ionic liquid and the wt % of ionic liquid determined by the difference in weight between the sample and the stripped residue.

The process of the invention employs a halide selected from chlorine, bromine and iodine compounds. Preferably, the halide is selected from bromine and iodine compounds that are vaporous under vapor phase carbonylation conditions of temperature and pressure. Suitable halides include hydrogen halides such as hydrogen iodide and gaseous hydroiodic acid; alkyl and aryl halides having up to about 12 carbon atoms such as methyl iodide, ethyl iodide, 1-iodopropane, 2-iodobutane, 1-iodobutane, methyl bromide, ethyl bromide, benzyl iodide and mixtures thereof. Desirably, the halide is a hydrogen halide or an alkyl halide having up to about 6 carbon atoms. Non-limiting examples of preferred halides include hydrogen iodide, methyl iodide, hydrogen bromide, methyl bromide and mixtures thereof. The halide may also be a molecular halogen such as $I_2$, $Br_2$ or $Cl_2$. The most preferred halide is iodide. Non-limiting examples of the most preferred vaporous halides include methyl iodide, hydrogen iodide and molecular iodine. The amount of vaporous halide present typically ranges from a molar ratio of about 1:1 to about 10,000:1 of alcohol, ether or ester equivalents to halide, with the preferred range being from about 5:1 to about 1000:1.

The process of the present invention is useful for any carbonylatable reactant. The term "carbonylatable reactant", as used herein, refers to one or more organic compound capable of reacting with carbon monoxide, under carbonylation conditions of temperature and pressure, to produce a carbonylation product resulting from the insertion of carbon monoxide into one or more chemical bonds. The carbonylatable reactant does not need to be totally soluble in the ionic liquid. Carbonylatable reactants include, but are not limited to, lower alkyl alcohols and their derivatives, including ethers, esters and mixtures of the same, and olefins containing up to 8 carbon atoms that can react with water, alcohols, aliphatic acids or carboxylic acids also present in the reactant stream under carbonylation process conditions to produce alcohols, ethers, esters, or alcohol derivatives in situ. Non-limiting examples of suitable carbonylatable reactants include alcohols, ethers and esters in which an aliphatic carbon is directly bonded to an oxygen atom of either an alcoholic hydroxyl group, an ether oxygen, or an ester oxygen. The carbonylatable reactant may include aromatic moieties. Preferably, the reactant is one or more lower aliphatic alcohols, ethers or esters having up to 10 carbon atoms and preferably up to 6 carbon atoms. More preferred reactants are methanol, dimethyl ether and methyl acetate. The most preferred reactant is methanol or combinations of dimethyl ether or methyl acetate with water.

Although the presence of water in the gaseous feed mixture is not essential when using methanol, the presence of some water is desirable to suppress formation of methyl acetate and/or dimethyl ether. When using methanol to generate acetic acid, the molar ratio of water to methanol can be about 0:1 to about 10:1, but preferably is in the range of about 0.01:1 to about 1:1. When using an alternative source of methanol such as methyl acetate or dimethyl ether, the amount of water fed usually is increased to account for the mole of water required for hydrolysis of the methanol alternative. Therefore, when using either methyl acetate or dimethyl ether, the mole ratio of water to ester or ether is in the range of about 1:1 to about 10:1, but preferably in the range of about 1:1 to about 3:1. In the preparation of acetic acid, it is apparent that combinations of methanol, methyl ester, and/or dimethyl ether are equivalent, provided the appropriate amount of water is added to hydrolyze the ether or ester to provide the methanol reactant. When the process is operated to produce methyl acetate, preferably no water should be added and dimethyl ether becomes the preferred feedstock. Further, when methanol is used as the feedstock in the preparation of methyl acetate, it is preferable to remove water.

The carbon monoxide may be fed to the carbonylation zone either as purified carbon monoxide or as carbon monoxide including other gases. The carbon monoxide need not be of high purity and may contain from about 1% by volume to about 99% by volume carbon monoxide, and preferably from about 70% by volume to about 99% by volume carbon monoxide. The remainder of the gas mixture may include such gases as nitrogen, hydrogen, water and parafinic hydrocarbons having from one to four carbon atoms. Although hydrogen is not part of the reaction stoichiometry, hydrogen may be useful in maintaining optimal catalyst activity. Therefore, the preferred ratio of carbon monoxide to hydrogen is in the range of about 99:1 to about 2:1, but ranges with even higher hydrogen levels are also useful. The amount of carbon monoxide useful for the carbonylation reaction ranges from a molar ratio of about 0.1:1 to about 1,000:1 of carbon monoxide to alcohol, ether or ester equivalents with a more preferred range being from about 0.5:1 to about 100:1 and a most preferred range from about 1.0:1 to about 20:1.

The process of this invention is operated in the vapor phase and, therefore, is practiced at temperatures above the dew point of the carbonylation product mixture. However, since the dew point is a complex function of dilution (particularly with respect to non-condensable gases such as unreacted carbon monoxide, hydrogen, or inert diluent gas), product composition, and pressure, the process may still be operated over a wide range of temperatures, provided the temperature exceeds the dew point of the product effluent.

The term "dew point", as used herein, means the temperature, at a given pressure, at which a gas is saturated with respect to its condensable components and at which condensation occurs. The dew point of the carbonylation products of the present invention may be calculated by methods well known to those skilled in the art, for example, as described in Perry's Chemical Engineer's Handbook, 6$^{th}$ ed, (McGraw-Hill), pp. 13–25 through 13–126. Dew points for single product or complex mixtures may be calculated using commercially available engineering computer programs, such as Aspen®, also well-known to those skilled in the art. In practice, the process typically operates at a temperature range of 100 to 250° C. Other examples of temperature ranges in which our process may operate include 120 to 240° C. and 150 to 240° C.

As with temperature, the pressure range is dependent, in part, upon the dew point of the product mixture. However, provided that the reaction is operated at a temperature sufficient to prevent liquefaction of the product effluent, a wide range of pressures may be used, e.g., pressures in the range of about 0.1 to about 100 bars absolute (bara). The process preferably is carried out at a pressure in the range of about 1 to about 50 bara and, most preferably, about 3 to about 30 bara.

The process of the present invention is carried out by contacting carbon monoxide, a carbonylatable reactant, and a halide with a non-volatile catalyst solution comprising an ionic liquid and a Group VIII metal, where the term "ionic liquid" means one or more organic salts which exist as a liquid under operating conditions and for the duration of the present process. The preferred ionic liquids in our process are known compounds and/or may be prepared according to published procedures. The ionic liquid should be reasonably thermally stable under the reaction conditions, and the catalytically active form of the Group VIII metal should be at least partially soluble in the ionic liquid. The ionic liquid can be transformed into another ionic liquid under the conditions of the reaction and still be suitable for the reaction. For example, a quaternary ammonium chloride may be converted to the corresponding quaternary ammonium iodide under carbonylation conditions employing an alkyl iodide as one of the vapor reactants. In general the anion of the ionic liquid should be the halide corresponding to the halogen contained in the vaporous halide promoter, althdugh this is not a requirement of the invention. The ionic liquid should have low or negligible vapor pressure under the reaction conditions to prevent its transport from the reaction zone. The ionic liquid can be a solid at room temperature but must melt at a temperature less than the temperature of the carbonylation reaction. Mixtures of two or more ionic liquids can be used. Solids normally not liquid at the temperature of the carbonylation reaction, such as lithium iodide, can be present as a soluble component of the ionic liquid. Organic salts suitable for use as ionic liquids are generally, but not limited to, ammonium, phosphonium or sulfonium salts. The salt can be formed in the reactor by the reaction of an amine, phosphine or sulfide with the alkyl halide vapor used in the carbonylation reaction. More preferred salts are quaternary ammonium or quaternary phosphonium salts. The most preferred salts are quaternary ammonium and phosphonium iodides.

Suitable quaternary ammonium and phosphonium iodides include, but are not limited to, iodide compound having the formula

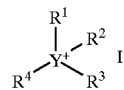

wherein $R^1$, $R^2$, $R^3$, and $R^4$ are independently selected from alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms; and Y is N or P. Quaternary ammonium iodides that may be used as ionic liquids are heterocyclic iodides having the formula

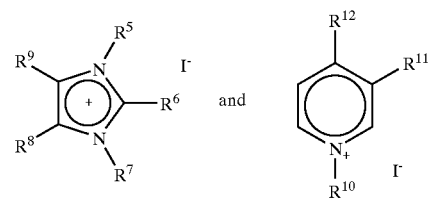

wherein at least one ring atom is a quarternary nitrogen atom and $R^6$, $R^8$, $R^9$, $R^{11}$, and $R^{12}$ are independently selected from hydrogen, alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms; and $R^5$, $R^7$, and $R^{10}$ are independently selected from alkyl or substituted alkyl moieties having up to about 20 carbon atoms, cycloalkyl or substituted cycloalkyl having about 5 to about 20 carbon atoms, or aryl or substituted aryl having about 6 to about 20 carbon atoms. Exemplary ammonium compounds include tetrapentylammonium iodide, tetrahexylammonium iodide, tetraoctylammonium iodide, tetradecylammonium iodide, tetradodecylammonium iodide, tetrapropylammonium iodide, tetrabutylammonium iodide, trioctylammonium iodide, N-octylquinuclidinium iodide, N,N'-dimethyl-N,N'-dihexadecylpiperazinium diiodide, dimethyl-hexadecyl-[3-pyrrolidinylpropyl]ammonium iodide, N,N,N,N',N',N'-hexa(dodecyl)octane-1,8-diammonium diiodide, N,N,N,N',N',N'-hexa(dodecyl)butane-1,4-diammonium diiodide; imidazolium iodides such as 1-butyl-3-methylimidazolium iodide, 1,3-dimethylimidazolium iodide, 1,3,4-trimethylimidazolium iodide, 1,2,3,4,5-pentamethylimidazolium iodide; pyridinium iodides such as N-octylpyridinium iodide, N-methylpyridinium iodide, N-methyl-3,4-lutidinium iodide; or mixtures thereof. Preferred quaternary ammonium iodides include 1-butyl-3-methylimidizolium iodide and 1,3-dimethylimidazolium iodide. Exemplary phosphonium compounds include tetraoctylphosphonium iodide, tetrabutylphosphonium iodide, triphenyl(hexyl)phosphonium iodide, triphenyl(octyl)-phosphonium iodide, tribenzyl (octyl)phosphonium iodide, tribenzyl(dodecyl) phosphonium iodide, triphenyl(decyl)-phosphonium iodide, triphenyl(dodecyl)phosphonium iodide, tetrakis(2-methylpropyl)phosphonium iodide, tris(2-methylpropyl) (butyl)phosphonium iodide, triphenyl(3,3-dimethylbutyl) phosphonium iodide, triphenyl(3-methylbutyl)phosphonium iodide, tris(2-methylbutyl)(3-methylbutyl)phosphonium iodide, triphenyl[2-trimethylsilylethyl]phosphonium iodide, tris(p-chlorophenyl)(dodecyl)phosphonium iodide, hexyltris (2,4,6-trimethylphenyl)phosphonium iodide, tetradecyltris (2,4,6-trimethylphenyl)phosphonium iodide, dodecyltris(2, 4,6-trimethylphenyl)phosphonium iodide, and the like.

Preferred phosphonium iodides include methyltriphenylphosphonium iodide, methyltributylphosphonium iodide, and butyltridodecylphosphonium iodide.

Another embodiment of our invention is a continuous process for preparing a carbonylation product selected from a carboxylic acid, a carboxylic acid ester, a carboxylic acid anhydride, or a mixture thereof comprising: (1) continuously feeding to a reaction zone carbon monoxide, a carbonylatable reactant selected from the group consisting of an alcohol, a dialkyl ether, and an alkyl carboxylic acid ester, and an iodide, wherein said carbon monoxide, carbonylatable reactant, and iodide are in the gas phase; (2) continuously contacting said carbon monoxide, carbonylatable reactant, and iodide of Step I with a non-volatile catalyst solution comprising about 50 to about 100 wt %, based on the total weight of the catalyst solution, of an ionic liquid selected from a quaternary ammonium salt, a quaternary phosphonium salt, and a tertiary sulfonium salt, and a Group VIII metal under steady state carbonylation conditions and at a temperature and pressure wherein the carbonylation product exits the reaction zone in the gas phase; and (3) continuously recovering from the reaction zone a gaseous effluent comprising the carbonylation product. The carbonylatable reactant is described previously, and the ionic liquid may be any quaternary ammonium or phosphonium salt as described and exemplified hereinabove.

In addition to an ionic liquid, the catalyst solution comprises one or more transition metals selected from Group VIII (Fe, Co, Ni, Ru, Rh, Pd, Os, Ir, Pt) of the periodic table. The form of the Group VIII metal is not critical and may be the elemental metal itself or one or more metal compounds. Non-limiting examples of Group VIII metal compounds which are generally satisfactory include those containing halide, trivalent nitrogen, organic compounds of trivalent nitrogen, carbon monoxide, hydrogen, carboxylate and 2,4-pentanedione, either alone or in combination. These are generally commercially available. Examples of suitable Group VIII species include but are not limited by rhodium trichloride hydrate, iridium trichloride hydrate, nickel iodide hydrate, palladium acetate and palladium chloride. Preferably the Group VIII metal species is at least partially dissolved in the ionic liquid under the reaction conditions. More preferably the Group VIII metal species is completely dissolved in the ionic liquid under the reaction conditions. Most preferably the Group VIII metal species is completely dissolved in the ionic liquid in a form that prevents it from being transported from the ionic liquid during the carbonylation reaction. Group VIII metal species include Rh, Ir, Ni, Co and Pd separately or in combination. When Ir is used, the catalyst solution may further comprise one or more promoters such as Re, Ru, Os, Pd or Pt, one or more Lewis acids, such as zinc iodide, in a molar amount about equivalent to or greater than the ionic liquid, or a combination of one or more promoters with one or more Lewis acids. Representative Lewis acids which may be used with Ir include compounds of Ga, In, Cd, Hg, Re, W and Mo. More preferred Group VIII metal species are Rh, Ir and Pd and the combination of Ir with Ru, Os, Pd or Pt. When Re, Ru, Os, Pd or Pt are used as promoters with Ir, the promoter/Ir molar ratio preferably ranges from about 0.1 to about 15 or more preferably from about 0.5 to about 10. The most preferred Group VIII metal species is Rh. The concentration of the Group VIII metal in the ionic liquid may vary considerably depending on the identities of the Group VIII metals and the ionic liquid and may range from about 0.0001 to about 1.0 molar. More preferred Group VIII metal concentrations range from about 0.001 to about 0.5 molar. Most preferred Group VIII concentrations range from about 0.005 to about 0.25 molar. When the metal is rhodium and the ionic liquid is 1-butyl-3-methylimidazolium iodide, Group VIII metal concentrations ranging from about 0.005 to about 0.05 molar are satisfactory.

Although various modes of operation are possible, the process of the invention is preferably operated as a continuous process. By "continuous" it is meant that the process is substantially or completely continuous in operation in contrast with a "batch" process. "Continuous" is not meant in any way to prohibit normal interruptions in the continuity of the process as a result of, for example, start-up, reactor maintenance or cleaning, purging of by-products or tars, or scheduled shutdown periods.

Generally the vapor is contacted with the base of a liquid contained in the reactor and allowed to pass upward through the liquid. Other methods can be utilized by those skilled in the art. For example, moving vapor in the upper region of the reactor may contact the liquid phase which is being stirred or otherwise agitated. The liquid may contact the vapor phase as a spray moving concurrently or counter currently to the vapor phase.

Our invention is useful for the preparation of acetic acid. Thus, our invention provides a continuous process for preparing acetic acid comprising: (1) continuously feeding to a reaction zone carbon monoxide, methyl alcohol, and methyl iodide, wherein said carbon monoxide, methyl alcohol, and methyl iodide are in the gas phase; (2) continuously contacting said carbon monoxide, methyl alcohol, and methyl iodide of Step I with a non-volatile catalyst solution comprising about 50 to about 100 wt %, based on the total weight of the catalyst solution, of an ionic liquid selected from a quaternary ammonium salt or a quaternary phosphonium salt, and rhodium while maintaining said reaction zone at a temperature of about 150 to about 240° C. and a pressure of about 3 bara to about 50 bara; and (3) continuously recovering from the reaction zone a gaseous effluent comprising acetic acid, methyl acetate, or a mixture thereof. The methyl alcohol and methyl iodide may be fed into the reaction zone in a molar ratio of about 5:1 to about 1,000:1 moles methyl alcohol:moles methyl iodide and the carbon monoxide and the methyl alcohol may be fed into the reaction zone in a molar ratio of about 1.0:1 to about 20:1 moles carbon monoxide:moles methyl alcohol. The ionic liquid may be any quaternary ammonium or phosphonium salt as described and exemplified hereinabove. Representative examples of ionic liquids are methyltributylphosphonium iodide, butyltridodecylphosphonium iodide, 1-butyl-3-methylimidazolium iodide, or 1,3-dimethylimidazolium iodide. In a further embodiment, the catalyst solution may comprise about 60 to about 100 wt % of an ionic liquid.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

EXAMPLES

The following is a general description of the reactor system and analytical methods used henceforward in Examples 1–15 unless otherwise specified. The reactor was constructed entirely of Hastelloy C alloy. Reactants entered the base of the reactor via a 0.375 inch (9.5 mm) outer diameter (O.D.) inlet tube having a wall thickness of 0.065 inch (1.65 mm). The portion above the inlet tube expanded as a collar piece as a cone into a cylindrical section having a 0.625-inch (1.60 cm) inner diameter (I.D.) and a wall thickness of 0.1875 inch (4.8 mm) with overall length of 2.00 inches (5.1 cm). The top 0.38-inch (9.7 mm) portion of the collar was machined to a diameter of 0.750 inch (1.9 cm). The machined portion of the collar contained a 0.735-inch (1.87 cm) diameter by 0.0625-inch (1.65 mm) thick Hastelloy C alloy 5 micron metal filter, which acted as a gas dispersion device and support for the ionic liquid. The filter and the collar containing the filter were welded to a 6.25-inch (15.9 cm) long by 0.625-inch (1.6 cm) I.D./0.750-inch (1.9 cm) O.D. Hastelloy C alloy reaction tube. The reaction tube was welded to an expanded zone increasing in a conical fashion at 45 degrees to an outer diameter of 1.50 inches (3.81 cm), continuing in a cylindrical fashion for another 1.83 inches (4.65 cm) and then decreasing at a 45-degree angle and welded to a 4.50 inch (11.4 cm) long by 0.375-inch (9.5 mm) O.D. loading and sensing tube. The vertical loading and sensing tube contained a 0.375-inch (9.5 mm) O.D. pressure transducer side arm located 2.0 inches (5.1 cm) above the expanded zone and positioned at 45 degrees from vertical of the loading and sensing tube. Vapor product was removed from the expanded zone through a 0.125 inch (3.18 mm) O.D. product removal line which extended up to approximately half the vertical distance of the expanded zone and off to one side. A Hastelloy C alloy 5 micron sintered metal filter was welded to the top end of the product removal line. The product removal line exited the expanded zone through the bottom conical portion of the expansion zone and continued downward to a distance past the base of the reactor inlet line.

Metered gas flows were maintained by Brooks 5850 Series E mass flow controllers interfaced with a Camile® 3300 Process Monitoring and Control System. Temperature control was also provided by the Camile® 3300 Process Monitoring and Control System. Liquid feed was provided by an Alltech 301 HPLC pump. Liquid and gas feeds were vaporized by feeding to a heated Hastelloy C alloy vaporizer maintained at 200° C. and transported in the vapor phase through a transfer line at 200° C. to the base of the reactor inlet tube. Heat to the reactor was provided by three separate split aluminum blocks with each split aluminum block surrounded by band heaters. Each split aluminum block heating unit had its own temperature control provided by the Camile® 3300 Process Monitoring and Control System. The bottom heater provided heat to the reactor inlet tube and collar piece. The central heater provided heat to the reaction tube section. The top heated provided heat to the expansion zone.

The end of the product removal line was connected to a Hastelloy C alloy condenser, which was attached to a Hastelloy C alloy product collection tank with a working capacity of one liter. The pressure was maintained using a Tescom Model 44-2300 backpressure regulator attached to a vent line on the top of product collection tank. Liquid samples were collected from a valve at the base of the liquid collection tank. Liquid products from the collection tank were weighed and analyzed by gas chromatography using a Hewlett Packard Model 6890 gas chromatograph fitted with a 30 m×0.25 mm DB-FFAP capillary column (0.25 micron film thickness) programmed at 40° C. for 5 minutes, 25° C./minute to 240° C. and holding at 240° C. for 1 minute using a thermal conductivity detector held at 250° C. (injector temperature=250° C.). The sample time shown in the tables, in hours, is the liquid sample collection time either from with the start of the reaction, as in sample 1, or from the end of the previous sample. Mixtures were prepared for gas chromatographic analysis by adding 5 mL of tetrahydrofuran solution containing 2 wt % decane internal standard to an accurately weighed 1 gram sample of the product mixture. Production rates are given as moles of products produced per liter of catalyst solution per hour and are calculated assuming the volume of the catalyst solution was 10 mL. Pressure is given in pounds per square inch gauge (psig) and in bars gauge (barg). It should be noted that bars absolute (bara) is equivalent to barg—1.01.

Example 1

This example illustrates the carbonylation of methanol in the presence of rhodium, 1-butyl-3-methylimidazolium iodide ionic liquid and water at elevated pressure utilizing the process of the invention. The reactor was loaded with the 1-butyl-3-methylimidazolium iodide (14.45 g, 10 mL), rhodium trichloride hydrate (83.7 mg, containing 40.01 wt % Rh) and water (2 mL) through the top of the reactor with carbon monoxide flowing at 50 standard cubic centimeters per minute (SCCM) through the base of the reactor. Carbon monoxide flows were maintained until the catalyst was removed from the reactor to prevent seepage of the liquid below the 5-micron sintered Hastelloy C alloy filter that acted as a gas dispersion and catalyst support device. A Hastelloy C alloy thermowell extending from the top of the reactor to the bottom 5-micron sintered Hastelloy C alloy filter was attached to the top of the vertical loading and sensing tube, and a pressure transducer was attached to the pressure transducer side arm. The system was pressurized to 200 psig (13.8 bars guage, barg) with 50 SCCM CO. The three reactor heaters were set for 180° C. After the reactor melt had reached 180° C. the CO flow was increased to 372 SCCM. A solution consisting of methanol/methyl iodide/water in a weight ratio of 67/29/4 was fed to the reactor system at 0.25 mL/minute. The density of the liquid feed system was 1.0 g/mL. The pressure in the reactor ranged between 200 and 210 psig (13.8 and 14.5 barg). After the liquid feed was started, the melt temperature increased to 192–194° C. and remained in that range. The results are reported in Table 1 wherein percent methanol (MeOH) conversion=100(moles methanol fed-moles methanol remaining)/(moles methanol fed). The moles of acetic acid (HOAc) produced per liter-hour and moles methyl acetate (MeOAc) produced per liter hour were calculated assuming that the volume of the catalyst solution was 10 mL.

TABLE 1

| Example Number | Sample Time, Hours | % MeOH Conversion | Production Rate (moles/L-hr) | |
|---|---|---|---|---|
| | | | HOAc | MeOAc |
| 1-1 | 6 | 92.6 | 14.4 | 5.3 |
| 1-2 | 15 | 95.2 | 17.7 | 5.8 |
| 1-3 | 9 | 94.9 | 18.0 | 5.7 |
| 1-4 | 15 | 94.4 | 17.9 | 5.3 |
| 1-5 | 8 | 92.8 | 17.8 | 5.5 |

No acetaldehyde, propionic acid or methyl propionate was detected.

Example 2

This example illustrates the carbonylation of methanol in the presence of rhodium, 1-butyl-3-methylimidazolium iodide ionic liquid in the absence of water at elevated pressure at various feed rates utilizing the process of the invention. The ionic liquid containing the rhodium catalyst used in Example 1 was retained in the reactor. The liquid feed consisted of methanol/methyl iodide in a weight ratio of 70/30 and had a density=1.0 g/mL. Liquid feed rate, carbon monoxide feed rate and the temperature of the ionic liquid (melt temp.) are provided in Table 2. Set temperatures and attained pressures were as per Example 1.

TABLE 2

| Example Number | mL Liquid Feed/Minute | SCCM CO | Melt Temp., °C. |
|---|---|---|---|
| 2-1 | 0.25 | 372 | 192 |
| 2-2 | 0.25 | 300 | 194 |
| 2-3 | 0.38 | 450 | 200 |
| 2-4 | 0.38 | 450 | 200 |
| 2-5 | 0.13 | 150 | 190 |
| 2-6 | 0.13 | 150 | 188 |
| 2-7 | 0.13 | 150 | 188 |
| 2-8 | 0.13 | 150 | 190 |
| 2-9 | 0.13 | 150 | 189 |
| 2-10 | 0.13 | 150 | 189 |
| 2-11 | 0.13 | 150 | 188 |
| 2-12 | 0.13 | 150 | 190 |
| 2-13 | 0.13 | 150 | 190 |

The corresponding methanol conversions, moles HOAc produced/L-hr and MeOAc produced/L-hr are provided in Table 3.

TABLE 3

| Example Number | Sample Time, Hours | % MeOH Conversion | Production Rate (moles/L-hr) | |
|---|---|---|---|---|
| | | | HOAc | MeOAc |
| 2-1 | 17.25 | 93.8 | 17.9 | 6.0 |
| 2-2 | 15 | 95.9 | 19.2 | 5.5 |
| 2-3 | 3 | 91.9 | 24.7 | 9.8 |
| 2-4 | 3 | 92.1 | 24.6 | 9.7 |
| 2-5 | 18 | 98.9 | 13.0 | 2.1 |
| 2-6 | 9 | 99.0 | 15.5 | 2.3 |
| 2-7 | 15 | 99.2 | 13.2 | 1.9 |
| 2-8 | 9 | 99.2 | 13.1 | 1.9 |
| 2-9 | 15 | 99.4 | 12.4 | 1.8 |
| 2-10 | 4 | 97.9 | 11.6 | 1.9 |
| 2-11 | 19 | 99.4 | 13.1 | 1.9 |
| 2-12 | 5 | 99.2 | 13.3 | 1.9 |
| 2-13 | 22 | 99.3 | 13.4 | 1.9 |

No acetaldehyde, propionic acid or methyl propionate was detected. The data from Example 2 show that water is not required for high rates and conversions and that excellent catalyst stability can be attained over a long period. Essentially no catalyst deactivation was observed.

Example 3

Example 3 illustrates the carbonylation of methanol in the presence of water at elevated pressure using an iridium catalyst dissolved in an ionic liquid consisting of 1-butyl-3-methylimidazolium iodide and zinc iodide. Zinc iodide (8.53 g), 1-butyl-3-methylimidazolium iodide (7.23 g), iridium trichloride hydrate (106.1 mg, 54.36 wt % Ir) and water (3 mL) were added to the reactor described in Example 1. The volume of the zinc iodide/1-butyl-3-methylimidazolium iodide mixture was 7 mL. The reactor was brought to reaction pressure and temperature as per Example 1. After the reactor melt had reached 180° C. the CO flow was increased to 300 SCCM. A solution consisting of methanol/methyl iodide/water in a weight ratios of 67/29/4 was fed to the reactor system at 0.25 mL/minute. The density of the liquid feed system was 1.0 g/mL. The pressure in the reactor ranged between 200 and 210 psig (13.8 and 14.5 barg). After the liquid feed was started, the melt temperature increased to 186–188° C. and remained in that range. The results are reported in Table 4.

TABLE 4

| Example Number | Sample Time, Hours | % MeOH Conversion | Production Rate (moles/L-hr) | |
|---|---|---|---|---|
| | | | HOAc | MeOAc |
| 3-1 | 3.5 | 53.5 | 7.6 | 4.2 |
| 3-2 | 19 | 28.4 | 0.7 | 3.4 |
| 3-3 | 6 | 29.1 | 0.6 | 3.2 |
| 3-4 | 19 | 27.7 | 0.5 | 3.2 |

The data in Table 4 reveal an initial high rate and conversion followed by a period of lower but steady rates and conversions.

Example 4

Example 4 illustrates the carbonylation of methanol in the absence of water at three different flow rates and at elevated pressure using the iridium catalyst dissolved in the ionic liquid consisting of 1-butyl-3-methylimidazolium iodide and zinc iodide. The ionic liquid containing the iridium catalyst used in Example 3 was retained in the reactor. The liquid feed consisted of methanol/methyl iodide in a weight ratio of 70/30 and had a density=1.0 g/mL. Liquid feed rate, carbon monoxide feed rate and the temperature of the ionic liquid (melt temp.) are provided in Table 5. Set temperatures and attained pressures were as per Example 3.

TABLE 5

| Example Number | mL Liquid Feed/Minute | SCCM CO | Melt Temp., °C. |
|---|---|---|---|
| 4-1 | 0.25 | 300 | 186 |
| 4-2 | 0.25 | 300 | 186 |
| 4-3 | 0.38 | 450 | 185 |
| 4-4 | 0.38 | 450 | 185 |
| 4-5 | 0.13 | 150 | 186 |
| 4-6 | 0.13 | 150 | 185 |
| 4-7 | 0.13 | 150 | 185 |
| 4-8 | 0.13 | 150 | 185 |
| 4-9 | 0.13 | 150 | 185 |
| 4-10 | 0.13 | 150 | 185 |
| 4-11 | 0.13 | 150 | 185 |
| 4-12 | 0.13 | 150 | 185 |
| 4-13 | 0.13 | 150 | 186 |

The corresponding methanol conversions, moles HOAc produced/L-hr and MeOAc produced/L-hr, are provided in Table 6.

TABLE 6

| Example Number | Sample Time, Hours | % MeOH Conversion | Production Rate (moles/L-hr) | |
|---|---|---|---|---|
| | | | HOAc | MeOAc |
| 4-1 | 5 | 24.3 | 0.5 | 3.5 |
| 4-2 | 18 | 30.3 | 0.3 | 3.3 |
| 4-3 | 3 | 25.6 | 0.3 | 3.9 |
| 4-4 | 3 | 21.3 | 0.3 | 3.8 |
| 4-5 | 3.5 | 41.4 | 0.3 | 2.0 |

TABLE 6-continued

| Example Number | Sample Time, Hours | % MeOH Conversion | Production Rate (moles/L-hr) | |
|---|---|---|---|---|
| | | | HOAc | MeOAc |
| 4-6 | 20.5 | 41.5 | 0.3 | 2.4 |
| 4-7 | 3.5 | 37.0 | 0.3 | 2.5 |
| 4-8 | 19 | 42.0 | 0.3 | 2.2 |
| 4-9 | 5 | 41.6 | 0.3 | 2.1 |
| 4-10 | 19 | 42.0 | 0.3 | 2.1 |
| 4-11 | 5 | 40.0 | 0.3 | 2.1 |
| 4-12 | 19 | 40.4 | 0.2 | 2.1 |
| 4-13 | 5 | 39.5 | 0.2 | 2.1 |

Comparison of the Examples 4-1 and 4-2 with Examples 3-2, 3-3 and 3-4 reveals essentially identical performance in the absence of water as in the presence of added water. The remaining data in Example 4 reveal the long-term stability of this iridium catalyst in the ionic liquid.

Example 5

This example illustrates the use of nickel dissolved in a melt consisting of a mixture of 1-butyl-3-methylimidazolium iodide and methyltriphenylphosphonium iodide at elevated pressure for the carbonylation of methanol in the presence of hydrogen and water. 1-butyl-3-methylimidazolium iodide (11.67 g), methyltriphenylphosphonium iodide (2.46 g), nickel iodide hexahydrate (0.883 g) and water (4 mL) were charged into the reactor described in Example 1. A solution consisting of water (1.3 g), methanol (1.3 g) and acetic acid (0.7 g) was used to rinse the residual solids into the reactor. The volume of the 1-butyl-3-methylimidazolium iodide/methyltriphenylphosphonium iodide/nickel iodide mixture was 10 mL. The reactor was brought to reaction pressure and temperature as per Example 1. After the reactor melt had reached 180° C. the CO flow was increased to 300 SCCM and 43 SCCM hydrogen was added to the gas mixture. A solution consisting of methanol/methyl iodide/water in a weight ratio of 67/29/4 was fed to the reactor system at 0.25 mL/minute. The density of the liquid feed system was 1.0 g/mL. The pressure in the reactor ranged between 200 and 210 psig (13.8 and 14.5 barg). After the liquid feed was started, the melt temperature increased to about 184° C. and remained at that value. The results are summarized in Table 7.

TABLE 7

| Example Number | Sample Time, Hours | % MeOH Conversion | Production Rate (moles/L-hr) | |
|---|---|---|---|---|
| | | | HOAc | MeOAc |
| 5-1 | 23.5 | 25.5 | 0.06 | 0.16 |
| 5-2 | 3.5 | 20.3 | 0.03 | 0.08 |
| 5-3 | 19.05 | 20.7 | 0.02 | 0.09 |

Example 6

This example illustrates the carbonylation of methanol using rhodium in 1,3-dimethylimidazolium iodide. The reactor described in Example 1 was charged with 1,3-dimethylimidazolium iodide (19.94 g, 10 mL), rhodium trichloride hyrdrate (83.7 mg, containing 40.01 wt % Rh), water (6.3 g), methanol (1.0 g) and acetic acid (1.5 g) through the top of the reactor with carbon monoxide flowing at 20 standard cubic centimeters per minute (SCCM) through the base of the reactor. The water, methanol and acetic acid were used to facilitate the loading of the other components into the reactor. The reactor was pressurized to 200 psig (13.8 barg) and heated to 180° C. The carbon monoxide feed rate was increased to 300 SCCM and the liquid feed consisting of methanol/methyl iodide in a weight ratio of 70/30 was fed at 0.25 mL/minute. The corresponding methanol conversions, moles HOAc produced/L-hr and MeOAc produced/L-hr are provided in Table 8.

TABLE 8

| Example Number | Sample Time, Hours | % MeOH Conversion | Production Rate (moles/L-hr) | |
|---|---|---|---|---|
| | | | HOAc | MeOAc |
| 6-1 | 3.63 | 92.8 | 9.43 | 3.64 |
| 6-2 | 19.5 | 97.2 | 16.69 | 4.79 |
| 6-3 | 4.5 | 96.7 | 18.61 | 5.16 |

Thus Example 6-3 when compared to Example 2-2 illustrates that 1,3-dimethylimidazolium iodide provides comparable rates and conversion as observed with 1-butyl-3-methylimidazolium iodide.

Example 7

This example illustrates the carbonylation of ethanol to ethyl propionate and propionic acid in the presence of rhodium and 1-butyl-3-methylimidazolium iodide. The reactor used in Example 1 was loaded as per Example 1 using 4 mL water instead of 2 mL water. After pressurizing to 200 psig (13.8 barg) and heating to 180° C., catalytic activity was established by first carbonylating methanol using the liquid feed consisting of methanol/methyl iodide in a weight ratio of 70/30 under the conditions used in Example 2-2 and then those used in Example 2-5. The methanol carbonylation was performed for 47.17 hours before switching to the ethanol-containing feed. Rates and conversions similar to those of Example 2 were observed. The liquid feed was then changed to a mixture consisting of ethanol/ethyl iodide in a weight ratio of 65.7/34.3 fed at 0.13 mL/minute. The feed had a density=1.0 g/mL. Carbon monoxide was fed at 150 SCCM. Samples 7-1, 7-2 and 7-3 were taken under these conditions. Sample 7-4 was taken with the furnace set at 190° C., the liquid feed at 0.06 mL/minute and the CO at 75 SCCM. The gas chromatograph conditions used to analyze the products were the same as those used in the previous examples. The results are summarized in Table 9.

TABLE 9

| Example Number | Sample Time, Hours | % Ethanol Conversion | Production Rate (moles/L-hr) | |
|---|---|---|---|---|
| | | | Propionic Acid | Ethyl Propionate |
| 7-1 | 9.93 | 74.2 | 0.80 | 0.85 |
| 7-2 | 17.42 | 65.8 | 1.16 | 1.25 |
| 7-3 | 24.58 | 65.9 | 1.13 | 1.25 |
| 7-4 | 19.67 | 93.0 | 1.49 | 0.79 |

Example 8

This example illustrates the production of acetic anhydride ($Ac_2O$) by the carbonylation of methyl acetate in the presence of rhodium and 1-butyl-3-methylimidazolium iodide. This example also illustrates that the catalyst system maintains good activity after being used for both ethanol and methyl acetate carbonylation. The reactor containing the catalyst system of Example 7 was used in this example. After the experiment of Example 7-4 was completed, the furnace temperature was lowered to 180° C., and the weight ratio methanol/methyl iodide=70/30 was fed at 0.13 mL/minute along with 150 SCCM CO for 5.33 hours. Pressure was maintained at 200 psig (13.8 barg). The gas feed was then changed to 150 SCCM CO and 8 SCCM hydrogen and a liquid feed consisting of methyl acetate/acetic acid/methyl iodide in a weight ratio of 65/21/14 having a density=1.0 g/mL was fed at 0.13 mL/minute. These conditions were maintained for a portion of an 18.83-hour time period before collecting the product samples shown in Table 10 due to a mechanical failure in the liquid feed pump although the CO-hydrogen flow was maintained at 200 psig (13.8 barg) during the entire 18.83 your period. The liquid feed pump was replaced before the samples in Table 10 were collected.

Liquid product samples were analyzed by gas chromatography. An accurately-weighed one-gram sample was diluted with 5 mL of an internal standard solution prepared from dilution of 20 mL p-xylene to 500 mL with acetonitrile. One microliter of this mixture was injected onto a 30M×0.25 mm×0.25 micron DB 1701 column under the following conditions using 14.5 psig (1 barg) helium carrier gas flowing at 3.0 mL/minute. Injector parameters: T=250° C., split flow=100 mL/minute, split ratio=75:1, purge=2 mL/minute; Detector parameters: flame ionization, T=250° C.; Oven parameters: 3 minutes at 35° C., 15° C./minute to 250° C., 250° C. for 0 minutes.

Examples 8-1 and 8-2 were performed with the furnace temperature at 180° C., liquid feed rate=0.13 mL/minute with gas flow rate=150 SCCM CO and 8 SCCM hydrogen. Example 8-3 was performed with the furnace temperature at 180° C., liquid feed rate=0.25 mL/minute and gas flow rate=300 SCCM CO and 15 SCCM hydrogen. Example 8-4 was performed with the furnace temperature at 190° C., liquid feed rate=0.25 mL/minute and gas flow rate=300 SCCM CO and 15 SCCM hydrogen. The results are summarized in Table 10.

TABLE 10

| Example Number | Sample Time, Hours | % MeOAc Conversion | Prod. Rate (moles/L-hr) Ac$_2$O |
|---|---|---|---|
| 8-1 | 3.17 | 63.3 | 0.2 |
| 8-2 | 18.8 | 27.1 | 1.0 |
| 8-3 | 5.0 | 20.2 | 1.3 |
| 8-4 | 19.5 | 20.8 | 1.4 |

The data in Table 10 reflect that steady state operation was achieved in Examples 8-2, 8-3 and 8-4 but not in 8-1.

After the sample of Example 8-4 was collected, the Furnace temperature was lowered to 180° C. and the weight ratio methanol/methyl iodide=70/30 was fed at 0.13 mL/minute along with 150 SCCM CO at 200 psig for 5.0 hours. The product was removed from the product collection tank, and the reaction was allowed to continue for an additional 18.0 hours. The methanol conversion was 99.6% and production rates of 9.1 moles HOAc/L-hr and 1.4 moles MeOAc/L-hr were measured. Thus the molten catalyst solution still had excellent methanol carbonylation activity after being used for methanol carbonylations in Examples 7 and 8, ethanol carbonylation in Example 7 and acetic anhydride carbonylation in Example 8.

Example 9

This example illustrates the production of acetic anhydride (Ac$_2$O) by the carbonylation of methyl acetate in the presence of palladium and 1-butyl-3-methylimidazolium iodide. The reactor of Example 1 was loaded with 1-butyl-3-methylimidazolium iodide (14.45 g, 10 mL) and a mixture of palladium acetate (73.1 mg, 0.325 mmol) dissolved in methyl acetate (3 mL). The reactor was pressurized to 200 psig (13.8 barg) with CO (20 SCCM) and heated to 180° C. The gas feed was then changed to 150 SCCM CO and 8 SCCM hydrogen and a liquid feed consisting of methyl acetate/acetic acid/methyl iodide in a weight ratio of 65/21/14 having a density=1.0 was fed at 0.13 mL/minute. Examples 9-1, 9-2, 9-3, and 9-4 were performed under these conditions. Example 9-5 was performed using the same gas and liquid feed rates at a 190° C. furnace temperature. Example 9-6 was performed at 190° C. in the absence of hydrogen with the carbon monoxide and liquid feed rates unchanged. The results are summarized in Table 11.

TABLE 11

| Example Number | Sample Time, Hours | % MeOAc Conversion | Prod. Rate (moles/L-hr) Ac$_2$O |
|---|---|---|---|
| 9-1 | 3.0 | 58.1 | 0 |
| 9-2 | 19.58 | 19.8 | 0.02 |
| 9-3 | 5 | 17.6 | 0.05 |
| 9-4 | 19 | 19.5 | 0.07 |
| 9-5 | 4.5 | 18.4 | 0.10 |
| 9-6 | 19.5 | 19.9 | 0.32 |

Example 10

This example illustrates the carbonylation of methanol in the presence of palladium and 1-butyl-3-methylimidazolium iodide. The reactor containing the catalyst system of Example 9 was used in this example. After experiment of Example 9-6 was completed, the furnace temperature was kept at 190° C., and the methanol/methyl iodide in a weight ratio of 70/30 was fed at 0.13 mL/minute along with 150 SCCM CO for 4 hours. Pressure was maintained at 200 psig (13.8 barg). The product was removed from the product collection tank, and the reaction was allowed to continue. Examples 10-1, 10-2, 10-3, 10-10-4 and 10-5 were performed at these conditions. Examples 10-6 and 10-7 were performed with the weight ratio methanol/methyl iodide=70/30 at 0.25 mL/minute along with 300 SCCM CO. The results are summarized in Table 12.

TABLE 12

| Example Number | Sample Time, Hours | % MeOH Conversion | Production Rate (moles/L-hr) | |
|---|---|---|---|---|
| | | | HOAc | MeOAc |
| 10-1 | 19.5 | 69.1 | 1.40 | 3.19 |
| 10-2 | 2.83 | 66.9 | 1.40 | 3.14 |
| 10-3 | 2.67 | 59.0 | 2.39 | 3.56 |
| 10-4 | 20.5 | 74.7 | 1.53 | 2.89 |
| 10-5 | 4.5 | 74.4 | 1.73 | 2.97 |
| 10-6 | 19.5 | 44.0 | 1.39 | 3.83 |
| 10-7 | 4.0 | 44.5 | 1.39 | 3.64 |

Example 11

This example illustrates the carbonylation of methanol in the presence of cobalt and 1-butyl-3-methylimidazolium iodide. The reactor of Example 1 was loaded with 1-butyl-3-methylimidazolium iodide (14.45 g, 10 mL) and a mixture of cobalt acetate tetrahydrate(498.2 mg, 2 mmoles) dissolved in water (3 mL). The reactor was pressurized to 200 psig (13.8 barg) with CO (20 SCCM) and heated to 190° C. The gas feed was then changed to 150 SCCM CO and 8 SCCM hydrogen and a liquid feed consisting of methanol/methyl iodide in a weight ratio of 70/30 was fed at 0.13 mL/minute. The reaction was performed under these conditions for 3.7 hours, and then the product was removed from the product collection tank. Examples 11-1 and 11-2 were performed under these same conditions. Example 11-3 was performed in the absence of hydrogen and at the same carbon monoxide and liquid feed rates. The results are shown in Table 13.

TABLE 13

| Example Number | Sample Time, Hours | % MeOH Conversion | Production Rate (moles/L-hr) | |
|---|---|---|---|---|
| | | | HOAc | MeOAc |
| 11-1 | 19.42 | 33.6 | 0.03 | 0.07 |
| 11-2 | 4.83 | 26.5 | 0.02 | 0.07 |
| 11-3 | 19.67 | 35.3 | 0.03 | 0.09 |

Example 12

This example illustrates the carbonylation of methanol in the presence of rhodium and 1-butyl-3-methylimidazolium iodide at one atmosphere pressure (1 bar absolute). This reaction was performed in a glass reactor. The reactor contained a coarse glass frit in a 15 mm ID (18 mm OD) glass tube that allowed gas to enter below the glass frit. The frit acted as a gas dispersion device and contained the ionic liquid above the frit when gas was flowing. The 15 mm ID glass tube extended upward beyond the frit an additional 5.5 inches (14 cm) and then expanded into a sphere with an inner diameter of 25 mm. The spherical region acted as an expansion zone to capture and return material entrained from the catalyst/ionic liquid mixture. The top of the spherical region was opened and connected to a 10 mm ID (12 mm OD) tube which continued to extend upward an additional 5 inches (12.7 cm) and was open at the top. A product removal tube of approximately 2 mm ID (3 mm OD) exited the side of the 10 mm ID tube at 0.4 inch (1 cm) above the top of the spherical region and angles downward toward the base of the reactor. The reactor effluent was condensed first at ambient temperature and then at −78° C.

The reactor was loaded with 1-butyl-3-methylimidazolium iodide (14.45 g, 10 mL), rhodium trichloride hydrate (83.7 mg, containing 40.01 wt % Rh) and water (4 mL) through the top of the reactor 10 mm tube with carbon monoxide flowing at 23 standard cubic centimeters per minute (SCCM) through the glass frit. The top of the reactor 10 mm tube was sealed with a rubber septum containing a 0.0625 inch (1.59 mm) OD stainless steel thermowell. The thermowell extended down into the reactor down to the glass frit. The Lindberg single element electric reactor furnace was slowly heated to 180° C., and the weight ratio methanol/methyl iodide=70/30 was fed at 0.02 mL/minute along with the 23 SCCM CO. Visual examination of the ionic liquid during the reaction revealed that it had a bulk liquid height of 56 mm and a foam head 4 mm thick. The temperature of the bulk liquid reaction zone was 172–173° C. and the foam head region was 176° C. The reaction was continued for 16 hours. The product was weighed and analyzed by gas chromatography as per Example 1. The methanol conversion was 46.0% and 0.05 moles acetic acid/L-hr and 0.27 moles methyl acetate/L-hr were produced. Thus the process of the invention is active for methanol carbonylation at relatively low pressure, low temperature and in the absence of added water.

Example 13

This example illustrates the carbonylation of methanol in the presence of rhodium and butyltridodecylphosphonium iodide. This example also illustrates that the carbonylation can be performed at CO/methanol molar ratio=1 without adversely affecting the rate and conversion. The reactor of Example 1 was loaded with butyltridodecylphosphomium iodide (9.44 g, 10 mL in the molten state above its melting point of 59–61° C.), rhodium trichloride hydrate (83.7 mg, containing 40.01 wt % Rh) and methanol (11 mL). The methanol was used to facilitate transfer of the other reagents. The reactor was pressurized to 200 psig (13.8 barg) with CO (20 SCCM) and heated to 180° C. The carbon monoxide feed rate was then increased to 150 SCCM, and the liquid feed consisting of methanol/methyl iodide in a weight ratio of 70/30 was fed at 0.13 mL/minute. The liquid feed rate was maintained throughout the entire course of the reaction, but the melt temperatures and gas feed rates were changed as shown in Table 14.

TABLE 14

| Example Number | Melt Temperature, ° C. | SCCM CO |
|---|---|---|
| 13-1 | 193 | 150 |
| 13-2 | 193 | 150 |
| 13-3 | 211 | 150 |
| 13-4 | 211 | 150 |
| 13-5 | 221 | 150 |
| 13-6 | 222 | 150 |
| 13-7 | 224 | 83 |
| 13-8 | 222 | 83 |
| 13-9 | 222 | 68 |
| 13-10 | 222 | 68 |
| 13-11 | 220 | 64 |
| 13-12 | 222 | 64 |

The corresponding methanol conversions and acetic acid and methyl acetate production rates are provided in Table 15.

TABLE 15

| Example Number | Sample Time, Hours | % MeOH Conversion | Production Rate (moles/L-hr) | |
|---|---|---|---|---|
| | | | HOAc | MeOAc |
| 13-1 | 3.75 | 29.9 | 1.19 | 2.84 |
| 13-2 | 19.25 | 70.8 | 2.29 | 4.31 |
| 13-3 | 4.75 | 83.0 | 5.07 | 4.54 |
| 13-4 | 19.83 | 87.1 | 5.61 | 4.40 |
| 13-5 | 5.08 | 90.4 | 7.51 | 4.19 |
| 13-6 | 19.0 | 91.7 | 8.00 | 3.91 |
| 13-7 | 5.67 | 97.0 | 10.67 | 2.77 |
| 13-8 | 18.42 | 96.9 | 11.56 | 3.00 |
| 13-9 | 5.08 | 96.8 | 10.08 | 3.41 |
| 13-10 | 23.58 | 96.8 | 9.76 | 3.58 |
| 13-11 | 21.08 | 96.4 | 8.79 | 3.83 |
| 13-12 | 22.42 | 97.9 | 9.85 | 3.32 |

In Examples 13-11 and 13-12 the molar feed rates of methanol and carbon monoxide were essentially the same.

Example 14

This example illustrates the carbonylation of methanol in the presence of rhodium and methyltributylphosphonium iodide. This example also illustrates that the process of the invention can operate at 100% methanol conversion and produce a product rich in acetic acid and low in water and methyl acetate. The reactor of Example 1 was charged with a solution of methyltributylphosphonium iodide (12.1 g) in methanol (2.5 g), rhodium trichloride hydrate (171.4 mg, containing 40.01 wt % Rh) and water (3 mL). The volume of the methyltributylphosphonium iodide on a methanol- and and water-free basis was 10 mL. The methanol and water were used to facilitate the loading of the other reactants into the reactor. The reactor was pressurized to 200 psig (13.8 barg) with CO (20 SCCM) and heated to 209° C. The carbon monoxide feed was then increased to 150 SCCM, and the weight ratio methanol/methyl iodide=70/30 liquid feed was fed at 0.13 mL/minute. The temperature of the molten reaction medium increased to about 220° C., and the upper portion of the reactor was maintained at 220° C. to ensure that acetic acid would not condense in the reactor. The reaction was run for 3.5 hours under these conditions to allow the reaction to come to steady state. Then the collection vessel was drained, and the samples of Examples 14-1, 14-2 and 14-3 were taken. The liquid feed rate was then decreased to 0.06 mL/minute, and the CO flow was reduced to 75 SCCM. The heater temperature was adjusted to maintain a melt temperature of about 220° C., and the reaction was run for 3.58 hours under these conditions to allow the reaction to come to steady state. Then the collection vessel was drained, and the sample of Example 14-4 was taken. The methanol conversion in all cases of Example 14 was 100%. Table 16 summarizes the results of Example 14 and includes the weight percent water found in the condensed product.

TABLE 16

| Example Number | Sample Time, Hours | Production Rate (moles/L-hr) HOAc | MeOAc | Wt % water in Product |
|---|---|---|---|---|
| 14-1 | 20.33 | 15.2 | 0.9 | 1.35 |
| 14-2 | 6.93 | 16.3 | 0.9 | 1.10 |
| 14-3 | 17.12 | 15.0 | 0.8 | 1.13 |
| 14-4 | 20.22 | 7.9 | 0.2 | 0.68 |

Example 15

This example illustrates the amount of reactants and products present in the ionic liquid medium under steady state operating conditions at two CO conversion levels. The reactor system used in this example is similar to that used in Example 1 except that a 300 mL Hastelloy C autoclave fitted with a dip tube, overhead stirrer and baffles was used instead of the original unstirred Hastelloy C reactor. A band heater heated the autoclave head, and a heated transfer line connected the autoclave to the condensation apparatus of Example 1. The reactant mixture was in the vapor state before contacting the catalyst solution in the autoclave.

The reactor was loaded with methyltributylphosphonium iodide (121 g, 100 mL), rhodium trichloride hydrate (837 mg, containing 40.01 wt % Rh) and methanol (100 mL). The methanol was used to facilitate transfer of the reagents. The reactor was pressurized to 228 psig (15.7 barg) with CO (60 SCCM) and heated to 220° C. The carbon monoxide feed rate was then set for 1500 SCCM, and the methanol/methyl iodide in a weight ratio of 70/30 was fed at 1.30 mL/minute. The reactor was operated in this fashion until the condensed vapor samples were of similar weights thereby indicating steady state conditions. The last two samples taken under these reaction conditions at one-hour intervals weighed 114.69 g (Sample A) and 115.68 g (Sample B) respectively. Sample A contained the following weight percentages by gas chromatographic analysis: 14.73 methyl iodide, 7.94 methyl acetate, 74.64 acetic acid, 0 methanol, 1.91 water. Sample B contained the following weight percentages by gas chromatographic analysis: 15.01 methyl iodide, 8.06 methyl acetate, 75.13 acetic acid, 0 methanol, 1.76 water. Carbon monoxide conversion (100×moles of acetyl produced/moles CO fed) was 39 percent for both Samples A and B. The liquid feed was stopped, and carbon monoxide (750 SCCM) was passed through the melt for one hour resulting in Sample C. Sample C is indicative of the amount of reactants and products present in the ionic liquid under steady state conditions although some additional carbonylation reaction may occur during the carbon monoxide purge. The weight of Sample C therefore represents an upper limit to the amount of reactants and products in the melt at steady state. Sample C (29.21 g) contained the following weight percentages by gas chromatographic analysis: 0.11 dimethyl ether, 3.10 methyl iodide, 2.31 methyl acetate, 95.65 acetic acid and 0.76 water.

The temperature was adjusted for 230° C., the carbon monoxide feed rate was then set for 938 SCCM, and the methanol/methyl iodide in a weight ratio of 70/30 was fed at 1.63 mL/minute. The reactor was operated in this fashion until the condensed vapor samples were of similar weights thereby indicating steady state conditions. The last three samples taken under these reaction conditions at one-hour intervals weighed 142.70 g (Sample D), 147.43 g (Sample E) and 142.86 g (Sample F) respectively. Sample D contained the following weight percentages by gas chromatographic analysis: 0.06 dimethyl ether, 17.40 methyl iodide, 12.98 methyl acetate, 67.32 acetic acid, 0.29 methanol, 2.79 water. Sample E contained the following weight percentages by gas chromatographic analysis: 0.07 dimethyl ether, 17.30 methyl iodide, 12.75 methyl acetate, 66.51 acetic acid, 0.30 methanol, 3.04 water. Sample F contained the following weight percentages by gas chromatographic analysis: 0.08 dimethyl ether, 17.14 methyl iodide, 12.82 methyl acetate, 67.82 acetic acid, 0.26 methanol, 3.03 water. Carbon monoxide conversion was 74–75 percent for the three samples. The liquid feed was continued for an additional 5 minutes, followed by a pure methanol feed at 1.63 mL/minute for two minutes while maintaining the carbon monoxide flow. Carbon monoxide (938 SCCM) was passed through the melt for one hour resulting in Sample G. Sample G also contains the products resulting from the 7 minutes of continued liquid feed in addition to those removed from the melt. Sample G (56.80 g) contained the following weight percentages by gas chromatographic analysis: 0.03 dimethyl ether, 8.42 methyl iodide, 5.13 methyl acetate, 85.95 acetic acid and 2.11 water.

We claim:

1. Continuous process for preparing a carbonylation product comprising:
   I. continuously feeding to a reaction zone carbon monoxide, a carbonylatable reactant, and a halide selected from chlorine, bromine, iodine and compounds thereof, wherein said carbon monoxide, carbonylatable reactant, and halide are in the gas phase;
   II. continuously contacting said carbon monoxide, carbonylatable reactant, and halide of Step I with a non-volatile catalyst solution comprising an ionic liquid and a Group VIII metal under steady state carbonylation conditions and at a temperature and pressure wherein said carbonylation product exits said reaction zone in the gas phase; and III. continuously recovering from said reaction zone a gaseous effluent comprising said carbonylated product.

2. Process according to claim 1 wherein said catalyst solution comprises about 25 to about 100 wt % of said ionic liquid based on the total weight of said catalyst solution.

3. Process according to claim 2 wherein said catalyst solution comprises about 50 to about 100 wt % of said ionic liquid based on the total weight of said catalyst solution.

4. Process according to claim 3 wherein said halide is hydrogen iodide, molecular iodine, or an alkyl or aromatic iodide and has up to 12 carbon atoms.

5. Process according to claim 4 wherein said carbonylatable reactant is selected from the group consisting of alcohols, ethers, and carboxylic acid esters and has up to 10 carbon atoms.

6. Process according to claim 5 wherein said carbonylatable reactant and said halide are fed into said reaction zone in a molar ratio of about 1:1 to about 10,000:1.

7. Process according to claim 6 wherein said carbon monoxide is about 1 volume % to about 99 volume % carbon monoxide and said carbon monoxide and said carbonylatable reactant are fed into said reaction zone in a molar ratio of about 0.5:1 to about 100:1.

8. Process according to claim 7 further comprising feeding hydrogen into said reaction zone in molar ratio to said carbon monoxide of about 1:99 to about 1:2.

9. Process according to claim 8 further comprising feeding water into said reaction zone in molar ratio to said carbonylatable reactant of about 0.01:1 to about 3:1.

10. Process according to claim 9 wherein said carbonylatable reactant further comprises olefins with up to 8 carbon atoms which react with water, alcohols, or carboxylic acids to form alcohols, ethers, or carboxylic esters under carbonylation process conditions.

11. Continuous process for preparing a carbonylation product selected from a carboxylic acid, a carboxylic acid ester, a carboxylic acid anhydride, or a mixture thereof comprising:
   I. continuously feeding to a reaction zone carbon monoxide, a carbonylatable reactant selected from the group consisting of an alcohol, a dialkyl ether, and an alkyl carboxylic acid ester, and an iodide, wherein said carbon monoxide, carbonylatable reactant, and iodide are in the gas phase;
   II. continuously contacting said carbon monoxide, carbonylatable reactant, and iodide of Step I with a non-volatile catalyst solution comprising about 50 to about 100 wt % of an ionic liquid, based on the total weight of said catalyst solution, selected from a quaternary ammonium salt, a quaternary phosphonium salt, and a tertiary sulfonium salt, and a Group VIII metal under steady state carbonylation conditions and at a temperature and pressure wherein said carbonylation product exits said reaction zone in the gas phase; and
   III. continuously recovering from said reaction zone a gaseous effluent comprising said carbonylation product.

12. Process according to claim 11 wherein said ionic liquid is an iodide compound having the formula

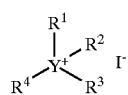

wherein $R^1$, $R^2$, $R^3$, and $R^4$ are independently selected from alkyl or substituted alkyl moieties with up to 20 carbon atoms, cycloalkyl or substituted cycloalkyl with 5 to 20 carbon atoms, or aryl or substituted aryl with 6 to 20 carbon atoms; and Y is N or P.

13. Process according to claim 11 wherein said ionic liquid is selected from the group consisting of heterocyclic iodides having the formula

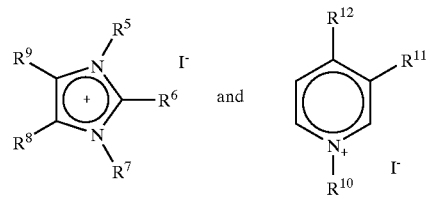

wherein at least one ring atom is a quarternary nitrogen atom and $R^6$, $R^8$, $R^9$, $R^{11}$, and $R^{12}$ are independently selected from hydrogen, alkyl or substituted alkyl moieties with up to 20 carbon atoms, cycloalkyl or substituted cycloalkyl with 5 to 20 carbon atoms, or aryl or substituted aryl with 6 to 20 carbon atoms; and $R^5$, $R^7$, and $R^{10}$ are independently selected from alkyl or substituted alkyl moieties with up to 20 carbon atoms, cycloalkyl or substituted cycloalkyl with 5 to 20 carbon atoms, or aryl or substituted aryl with 6 to 20 carbon atoms.

14. Process according to claim 11 wherein said Group VIII metal is selected from Rh, Ir, Ni, Co, Pd, or combinations thereof.

15. Process according to claim 14 wherein the molar concentration of said Group VIII metal in the ionic liquid is about 0.0001 molar to about 1.0 molar.

16. Process according to claim 15 wherein said Group VIII metal is Ir and said catalyst solution further comprises at least one metal promoter selected from the group consisting of Re, Ru, Os, Pd, and Pt, wherein the molar ratio of said metal promoter to said Ir is about 0.1 to about 15.

17. Process according to claim 16 wherein said catalyst solution further comprises at least one Lewis acid selected from the group consisting of compounds of Zn, Ga, In, Cd, Hg, W, and Mo, wherein the molar ratio of said Lewis acid to said ionic liquid is at least 1:1.

18. Process according to claim 15 wherein said Group VIII metal is Ir and said catalyst solution further comprises at least one Lewis acid selected from the group consisting of compounds of Zn, Ga, In, Cd, Hg, Re, W, and Mo, wherein the molar ratio of said Lewis acid to said ionic liquid is at least 1:1.

19. Continuous process for preparing acetic acid comprising:
   I. continuously feeding to a reaction zone carbon monoxide, methyl alcohol, and methyl iodide, wherein said carbon monoxide, methyl alcohol, and methyl iodide are in the gas phase;
   II. continuously contacting said carbon monoxide, methyl alcohol, and methyl iodide of Step I with a non-volatile catalyst solution comprising about 50 to about 100 wt % of an ionic liquid, based on the total weight of said catalyst solution, selected from a quaternary ammonium salt or a quaternary phosphonium salt, and rhodium while maintaining said reaction zone at a temperature of about 150 to about 240° C. and a pressure of about 3 bara to about 50 bara; and
   III. continuously recovering from said reaction zone a gaseous effluent comprising acetic acid, methyl acetate, or a mixture thereof.

20. Process according to claim 19 wherein said methyl alcohol and said methyl iodide are fed into said reaction zone in a molar ratio of about 5:1 to about 1,000:1 and wherein the said carbon monoxide and said methyl alcohol are fed into said reaction zone in a molar ratio of about 1.0:1 to about 20:1.

21. Process according to claim 20 wherein said ionic liquid is methyltributylphosphonium iodide, butyltridodecyiphosphonium iodide, 1-butyl-3-methylimidazolium iodide, or 1,3-dimethylimidazolium iodide.

22. Process according to claim 21 wherein said catalyst solution comprises about 60 to about 100 wt % of said ionic liquid, based on the total weight of said catalyst solution.

* * * * *

UNITED STATES PATENT AND TRADEMARK OFFICE
CERTIFICATE OF CORRECTION

PATENT NO. : 6,916,951 B2
DATED : July 12, 2005
INVENTOR(S) : Tustin et al.

It is certified that error appears in the above-identified patent and that said Letters Patent is hereby corrected as shown below:

Column 25,
Line 8, "butyltridodecyiphosphonium" should be -- butyltridodecylphosphonium --.

Column 26,
Line 1, "butyltridodecyiphosphonium" should be -- butyltridodecylphosphonium --.

Signed and Sealed this

Twenty-seventh Day of September, 2005

JON W. DUDAS
*Director of the United States Patent and Trademark Office*